United States Patent [19]

Kragl et al.

[11] Patent Number: 5,071,750

[45] Date of Patent: Dec. 10, 1991

[54] ENZYMATIC PROCESS FOR PREPARING N-ACETYLNEURAMINIC ACID

[75] Inventors: Udo Kragl; Christian Wandrey, both of Juelich, Fed. Rep. of Germany; Oreste Ghisalba, Reinach; Daniel Gygax, Himmelried, both of Switzerland

[73] Assignees: Forschungszentrum Juelich GmbH, Juelich, Fed. Rep. of Germany; Ciba-Geigy Corporation, Ardsley, N.Y.

[21] Appl. No.: 606,944

[22] Filed: Oct. 31, 1990

[30] Foreign Application Priority Data

Nov. 15, 1989 [DE] Fed. Rep. of Germany ....... 3937891

[51] Int. Cl.$^5$ .......................... C12P 7/58; C12N 9/88; C12N 9/90; C07H 7/033
[52] U.S. Cl. ........................................ 435/94; 435/85; 435/232; 435/233
[58] Field of Search .................. 435/94, 84, 233, 232, 435/85, 137, 128, 42, 813

[56] References Cited

U.S. PATENT DOCUMENTS 4,960,701 10/1990 Horiuchi et al. ..................... 435/190

FOREIGN PATENT DOCUMENTS 2278982 12/1987 Japan ................................... 435/232

OTHER PUBLICATIONS

Sahamoy Ghosh and Saul Roseman, "The Sialic Acids, V.N-Acyl-D-Glucosamine 2-Epimerase", The Journal of Biological Chemistry, vol. 240, No. 4, Apr. 1965, pp. 1531–1536.
Asis Datta, "N-Acetylglucosamine 2-Epimerase from Hog Kidney", Carbohydrate Metabolism, vol. XLI, Part B, 1975, pp. 407–412.
Subramaniam Sabesan and James C. Paulson, "Combined Chemical and Enzymatic Synthesis of Sialyloligosaccharides and Characterization by 500 MHz $^1$H and $^{13}$C NMR Spectroscopy", *J. Am. Chem. Soc.*, 108, 1986, pp. 2068–2080.
Roland Schauer, "Chemistry, Metabolism and Biological Functions of Sialic Acids", *Advances in Carbohydrate Chemistry and Biochemistry*, vol. 40, 1982, pp. 131–234.
Donald G. Comb and Saul Roseman, "The Structure and Enzymatic Synthesis of N-Acetylneuraminic Acid", *Journal of Biological Chemistry*, vol. 235, No. 9, Sep. 1960, pp. 2529–2537.
Mahn-Joo Kim, William J. Hennen, H. Marcel Sweers, and Chi-Huey Wong, "Enzymes in Carbohydrate Synthesis: N-Acetylneuraminic Acid Aldolase Catalyzed Reactions and Preparation of N-Acetyl-2-deoxy-D-neuraminic Acid Derivatives", *J. Am. Chem. Soc.*, 110, 1988, 6481–6486.
Claudine Augé, Bénédicte Bouxom, Bertrand Cavayé and Christine Gautheron, "Scope and Limitations of the Aldol Condensation Catalyzed by Immobilized Acylneuraminate Pyravute Lyase", *Tetrahedron Letters*, vol. 30, No. 17, 1989, pp. 2217–2220.

Primary Examiner—Herbert J. Lilling
Attorney, Agent, or Firm—Foley & Lardner

[57] ABSTRACT

A process for obtaining N-acetylneuraminic acid from N-acetylglucosamine is disclosed. The process is carried out in a reactor which contains both N-acylglucosamine-2-epimerase (E.C. 5.1.3.8) which isomerizes GlcNac into ManNac, and N-acetylneuraminic acid pyruvate lyase (E.C. 4.1.3.3) which catalyzes the reaction of the resulting ManNac with pyruvic acid to give Neu5Ac. GlcNAc and Pyr are fed into the reactor and Neu5Ac is obtained in the outflow. The process is preferably carried out continuously and in particular in an enzyme membrane reactor at pH 7.5 and 25° C., especially using residence times of 0.2 to 10 h, and with an excess of GlcNac in comparison with Pyr which is subsequently added if necessary. Epimerase and lyase are preferably present in the reactor in a ratio of activities which is equivalent to the reciprocal value of the quotient of the conversion rates.

9 Claims, 6 Drawing Sheets

ManNAc + Pyr → Nec 5 Ac
pH 7,5

ENZYMATIC PROCESS FOR PREPARING N-ACETYLNEURAMINIC ACID

BACKGROUND OF THE INVENTION

The present invention relates to a process for preparing N-acetylneuraminic acid. More particularly, it relates to a process comprising isomerization of N-acetylglucosamine, in the presence of N-acylglucosamine-2-epimerase (E.C. 5.1.3.8), to give N-acetylmannosamine which is then reacted with pyruvic acid in the presence of N-acetylneuraminic acid pyruvate lyase (E.C. 4.1.3 3) to give N-acetylneuraminic acid.

N-acetylneuraminic acid (abbreviated as Neu5Ac in the following) is the most important representative of the sialic acid class of substances. Sialic acids occupy the terminal positions of glycolconjugates such as glycolipids and glycoproteins which are, for example, on the cell surfaces and carry out important functions in the differentiation, maturation and intracellular interaction of cells. The synthesis of short-chain oligosaccharides having terminal sialic acids, in particular Neu5Ac, is gaining more and more interest in this connection. The treatment of cancers by Neu5Ac derivatives has also been reported (see S. Sabesan et al., *J. Am. Chem. Soc.* 108: 2068-2080 (1986); R. Schauer, *R. Adv. Carbohvdr. Chem. Biochem.* 40: 131-234 (1982)).

Neu5Ac has hitherto been isolated from natural sources (cow's milk, swallows' nests; c.f. Schauer, ibid.). However, the availability of these sources is limited and the purification is difficult and time-consuming because of the large number of sialic acids present therein.

The enzymatic synthesis of Neu5Ac from N-acetylmannosamine and pyruvic acid (hereinafter abbreviated as ManNAc and Pyr, respectively) has been known since the 1960s (Comb et al., *J. Biol. Chem.* 235: 2529-2537 (1960)). The enzyme used is N-acetylneuraminic acid pyruvate lyase (E.C. 4.1.3.3), hereinafter referred to as lyase. During this process the following reaction takes place:

Recent papers (M.-J. Kim et al., *J. Am. Chem. Soc.* 110: 6481-6486 (1988) and C. Auge et al., *Tetrahedron Letters* 30: 2217-2220 (1989)) report the synthesis of Neu5Ac, in which the lyase is used in immobilized form covalently coupled to insoluble carriers (PAN or agarose). With this form of immobilization, losses of activity due to the coupling are observed. A continuous production using enzyme which has been immobilized on a carrier is only possible when agents having antibacterial action are added.

The starting material for this N-acetylneuraminic acid formation is the relatively expensive N-acetylmannosamine. Availability of this starting material from N-acetylglucosamine (GlcNAc) has been mentioned in the paper by M.J. Kim referred to above. This paper considers the possibility of obtaining ManNAc by an isomerization of GlcNAc catalyzed by bases with the formation of ManNAc by a chemical method or by an isomerization of GlcNAc to ManNAc catalyzed by epimerase. No concrete data whatsoever are given, although the epimerase and its usefulness for the conversion of GlcNAc into ManNAc were known (see Ghosh et al., *J. of Biol. Chem.* 240: 1531-6 (1965)).

SUMMARY OF THE INVENTION

It is therefore an object of the present invention to provide a process which, on the one hand, uses the less expensive GlcNAc as starting material and, on the other hand, makes it possible to avoid any intermediate separations and preferably avoid decreases in activity.

In accomplishing these and other objects, there is provided a process for preparing N-acetylneuraminic acid, comprising the steps of (a) isomerizing N-acetylglucosamine in a reactor, in the presence of N-acylglucosamine-2-epimerase (E.C. 5.1.3.8), to give N-acetylmannosamine, and (b) reacting the N-acetylmannosamine with pyruvic acid in the presence of N-acetylneuraminic acid pyruvate lyase (E.C. 4.1.3.3) in the same reactor to give N-acetylneuraminic acid, wherein both the epimerase and the lyase are present in a reactor simultaneously, and steps (a) and (b) occur simultaneously.

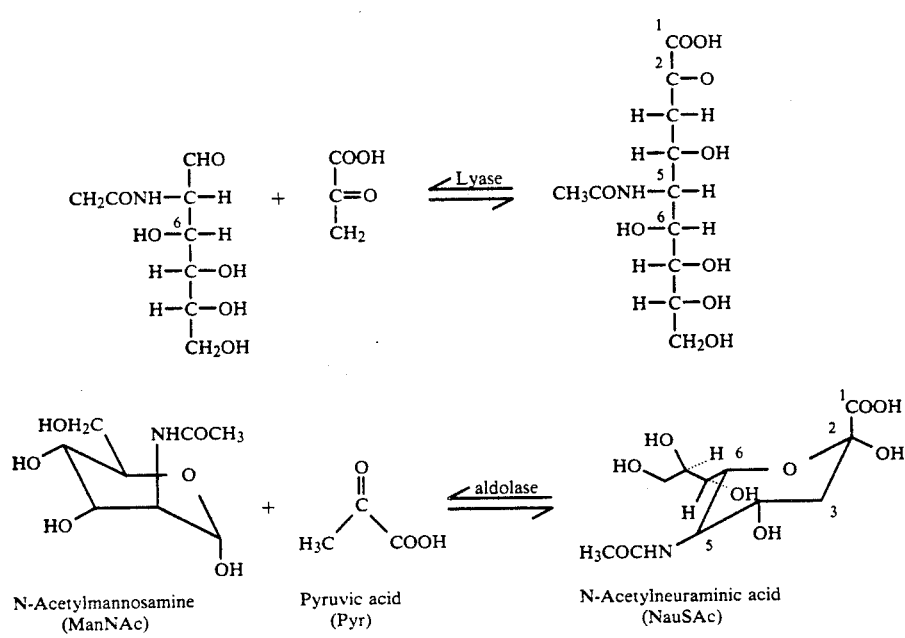

N-Acetylmannosamine (ManNAc)

Pyruvic acid (Pyr)

N-Acetylneuraminic acid (NauSAc)

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The process according to the invention comprises bringing about the formation of N-acetylneuraminic acid in a reactor containing both the epimerase and the lyase into which N-acetylglucosamine and pyruvate are fed and from the outflow of which N-acetylneuraminic acid is obtained.

In a sophisticated way, the process is based on the fact that GlcNAc is not converted by the lyase and that the latter is relatively inexpensive and can therefore be employed under conditions which are not the optimum conditions for the activity of lyase. It is also based on the similarity of the stability and pH optimums of the two enzymes. By optimizing the reaction conditions it is possible to adjust the activities of the two enzymes, the epimerase and the lyase, to one another and, for example, diminish the inhibiting effect of pyruvate on the epimerase by reduced pyruvate concentrations. The pyruvate present in the reaction system represents a considerable excess in comparison with the developing ManNAc, even when there are relatively low concentrations, so that the conversion into Neu5Ac takes place smoothly with ManNAc being consumed, promoting its formation from GlcNAc.

Suitable concentrations in the reactor are 50-500 mMol of GlcNAc/l, in particular about 200 mMol of GlcNAc/l, and 30-200 mMol of pyruvate/l, in particular about 50-150 mMol of pyruvate/l, especially around about 80 mMol of pyruvate/l.

The process is preferably carried out in a continuous manner and, in particular, in an enzyme membrane reactor.

In the enzyme membrane reactor (EMR), the enzymes are present in the soluble form and are retained by an ultrafiltration membrane which is located in front of the reactor outlet having an appropriate cut-off. Immobilization on a carrier, together with corresponding decreases in activity, is therefore not necessary. It is possible to sterilize the reactor before starting the operation so that the addition of agents having antibacterial action can be eliminated.

Since the EMR operates under outflow conditions, it is also possible to dispense with the use of buffer substances if the pH of the inflow is adjusted accordingly.

Dispensing with these substances facilitates the subsequent isolation of the products which is carried out in analogy with described processes (cf. R. Schauer ibid).

Figure 1:
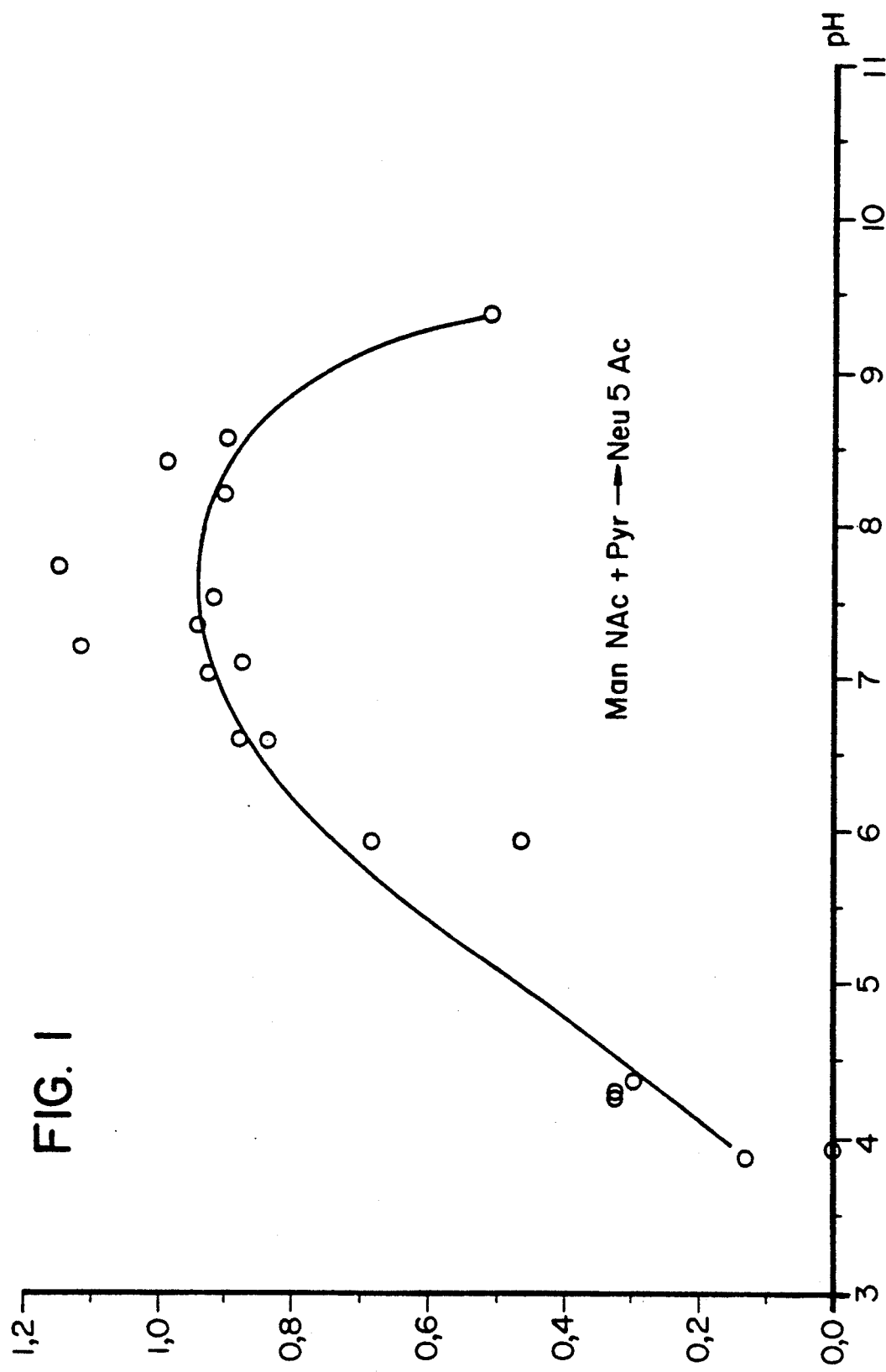
FIGS. 1, 2 and 4 are curves of the relative activity of the enzymes as a function of the pH.

Employing both the epimerase and lyase in the same, i.e., single stage, reaction system makes it necessary to select reaction conditions which are adjusted to the enzymatic activity of both enzymes. The pH dependence of the enzymatic reactions both for the Neu5Ac formation by means of lyase and for the ManNAc formation by means of epimerase was analyzed first. FIGS. 1 and 2 show the curves found for 25° C, which indicate that a pH selected in the neutral range (pH 7) is advantageous for both reactions.

Figure 3:
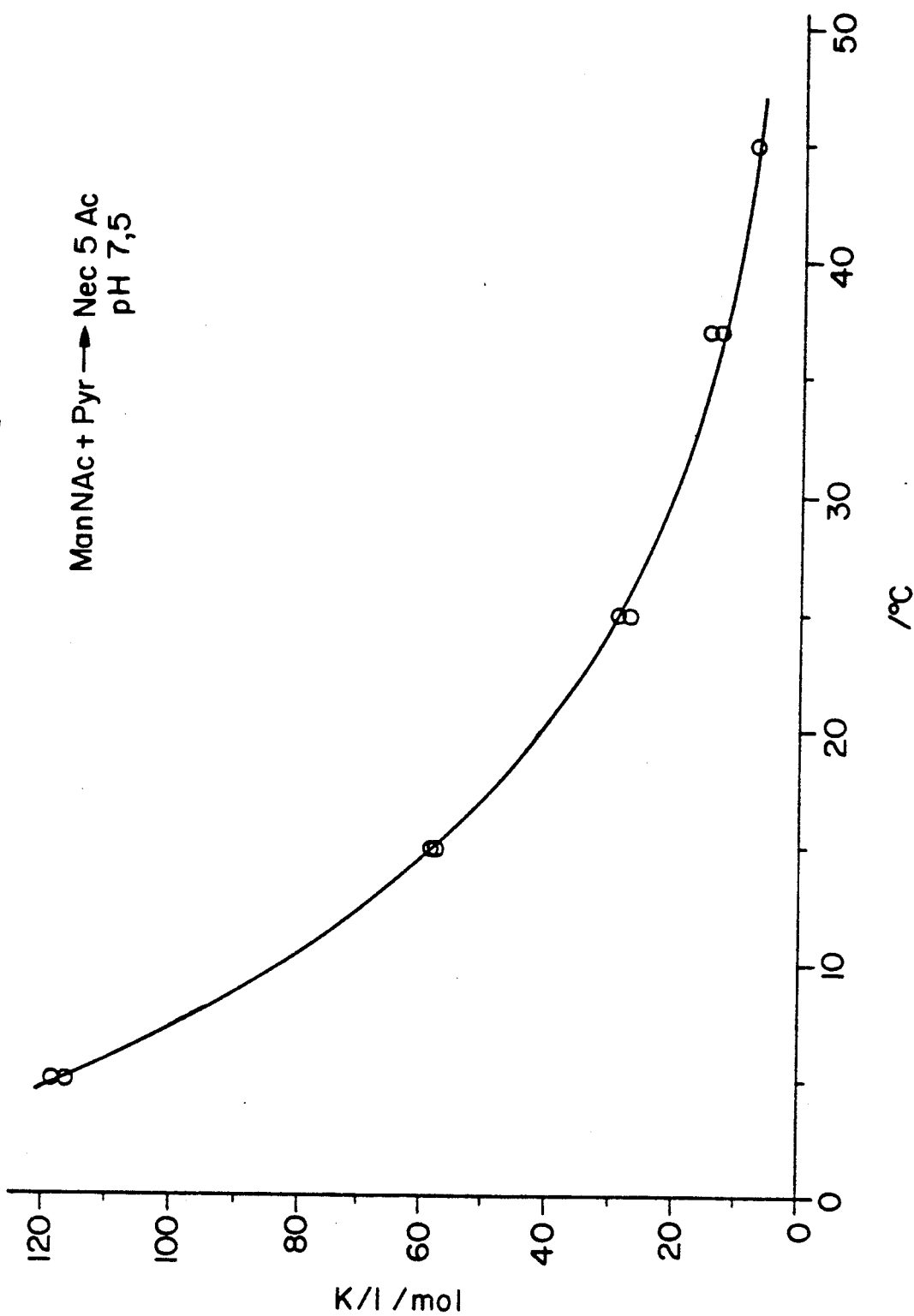
FIG. 3 shows the equilibrium constant of the Neu5Ac formation as a function of the temperature.

The analysis of the temperature dependence of the equilibrium constant of the Neu5Ac formation at pH 7.5 (see FIG. 3) showed that temperatures as low as possible should be useful in principle; however, since a significant decrease in enzymatic activity occurs at low temperatures (of, for example, 10° C.) and the mutarotation effects of the sugars ($\alpha$-anomer $\rightleftarrows \beta$-anomer), which, as preceding reactions, determine the conversion rate, take place more slowly at low temperatures, operations at around 25° C. appear to be more appropriate.

Figure 2A:
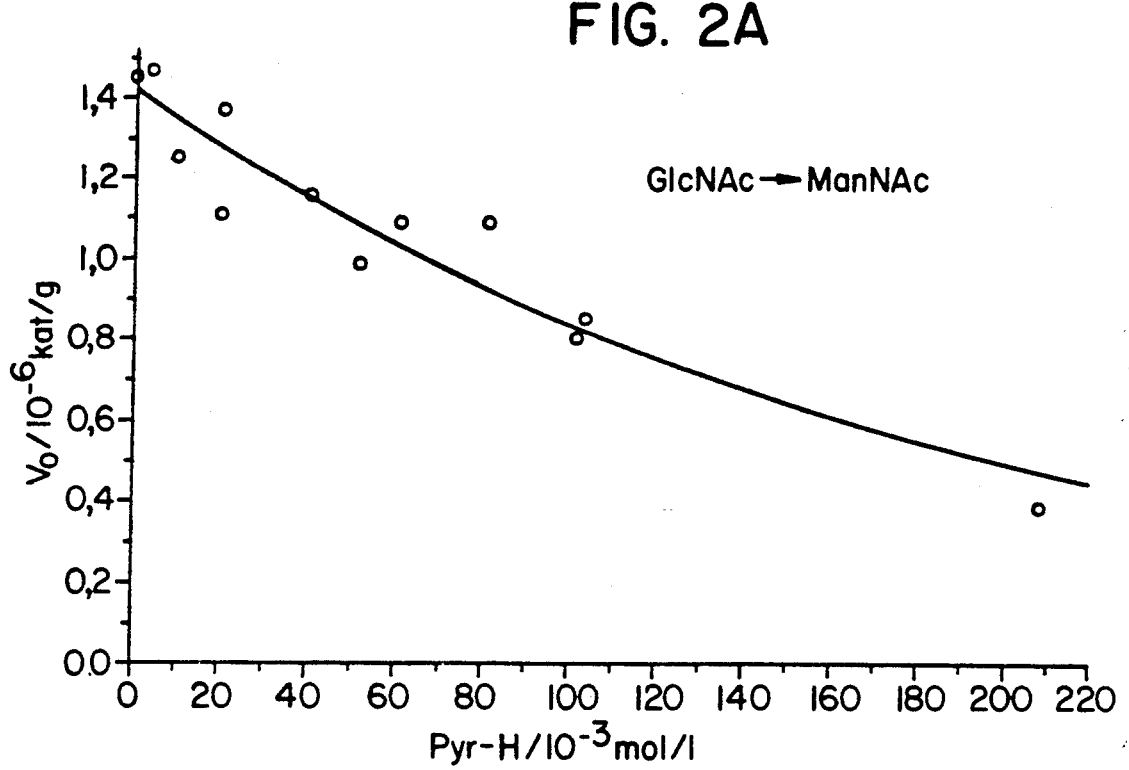
FIG. 2A shows the relative activity of the epimerase as a function of the pyruvate concentration.
Figure 2:
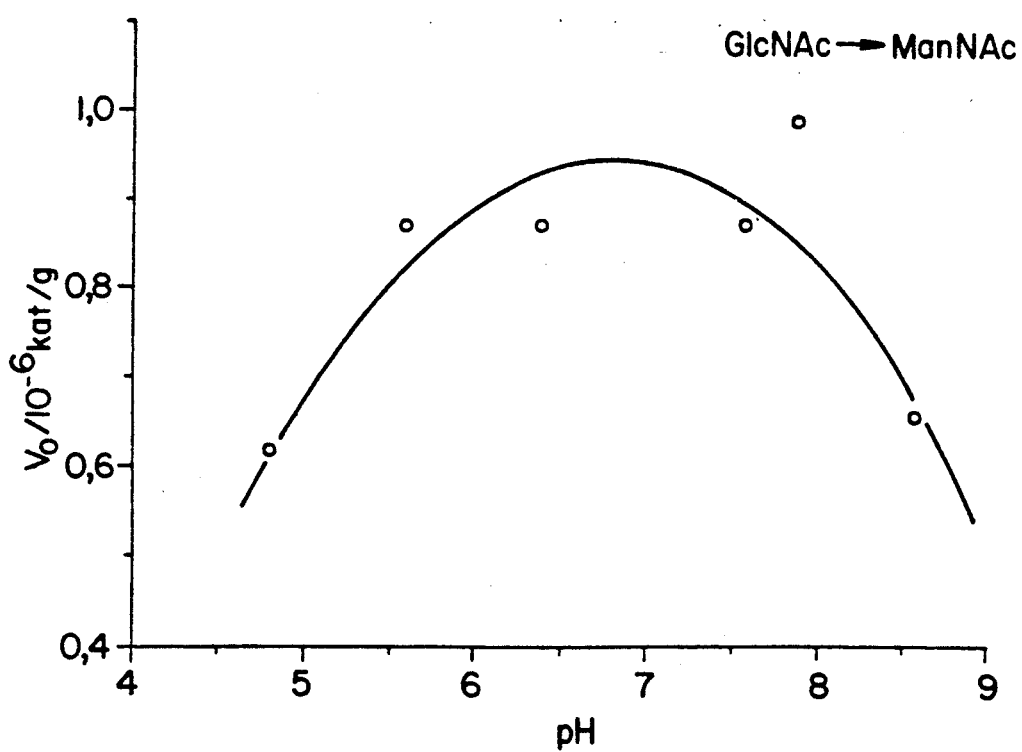

As FIG. 2A shows, the isomerization of GlcNAc to ManNAc is increasingly inhibited by pyruvic acid as that concentration increases. Further experiments showed that N-acetylneuraminic acid, the desired product, also has an inhibiting effect on the epimerase.

GlcNAc and pyruvate are fed into the EMR for the two-step synthesis taking place in the same reaction system. In the presence of the epimerase and lyase in the reactor, a conversion of GlcNAc into ManNAc by means of acylglucosamine 2-epimerase (E.C.5.1.3.8; Datta, METHODS IN ENZYMOLOGY 4I: 407-411 (1975)) initially takes peace then in accordance with the following equation:

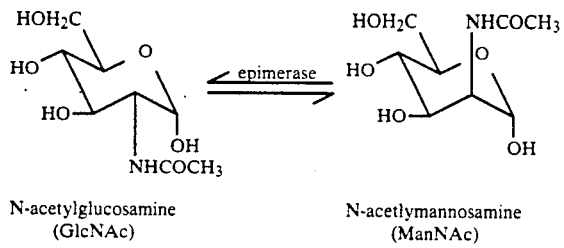

N-acetylglucosamine (GlcNAc)  N-acetlymannosamine (ManNAc)

Figure 4:
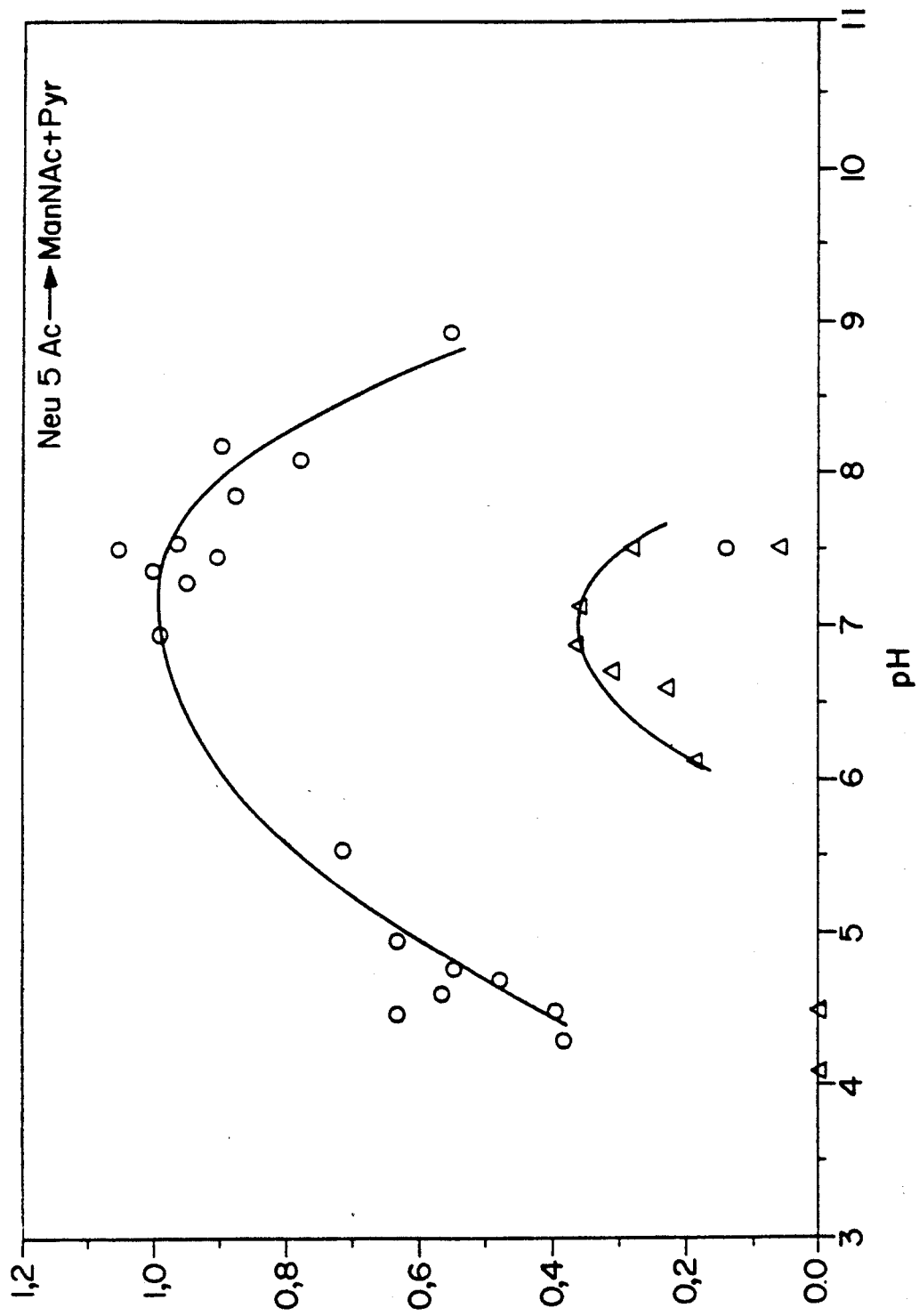
Figure 5:
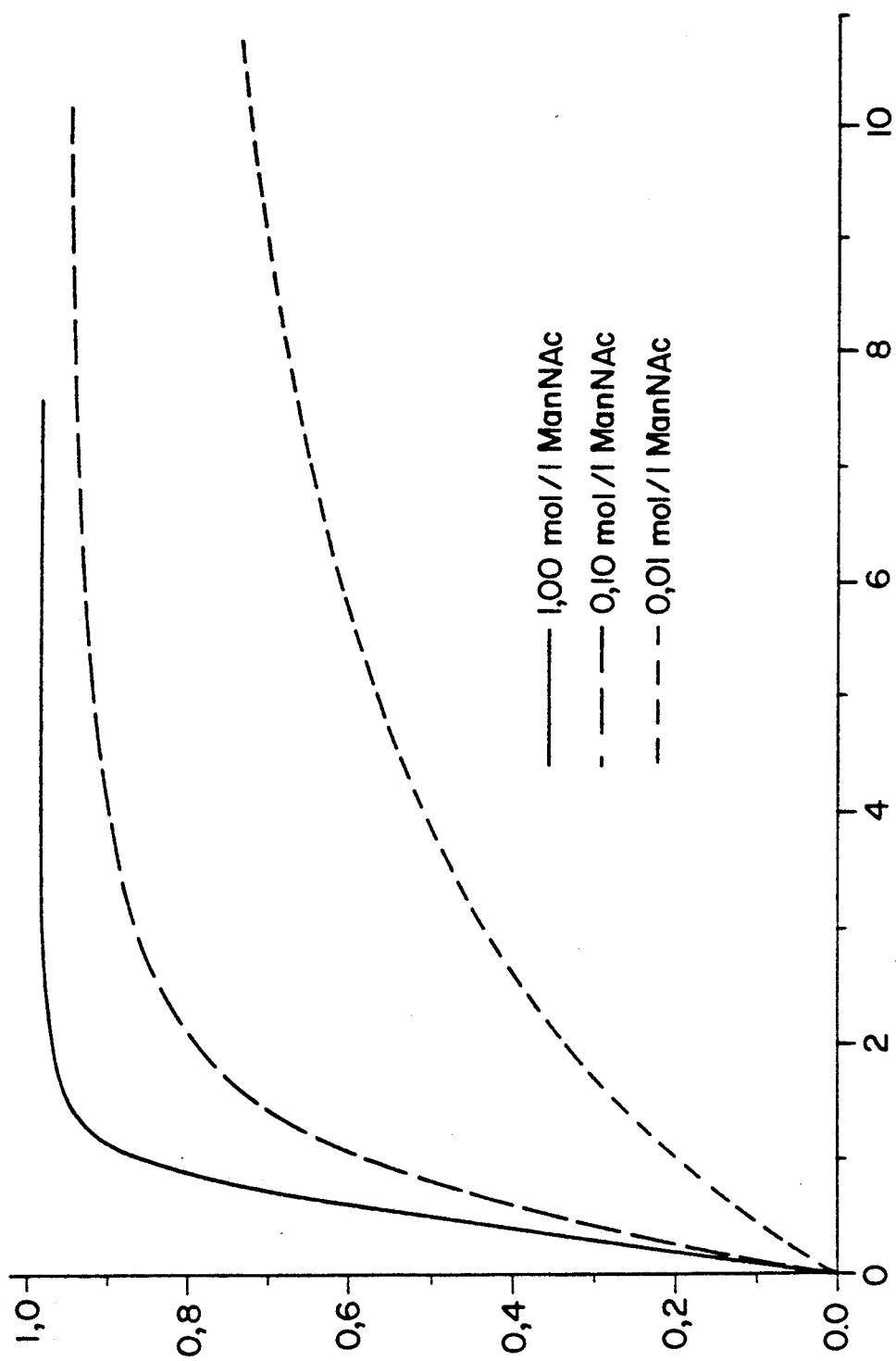
FIG. 5 shows the equilibrium conversion as a function of the Pyr/ManNAc ratio for various ranges of ManNAc concentrations.

Because of the large excess of pyruvate, subsequent conversion of the ManNAc to Neu5Ac is promoted. The reverse reaction is strongly inhibited by the amount of pyruvate, a considerable excess of which is present in comparison with the Neu5Ac formed, as can be seen from FIG. 4. FIG. shows that the amount of pyruvate, a large excess of which is naturally present in the reaction system according to the invention, promotes the shift of the equilibrium constant of the Neu5Ac formation towards higher values.

Since the isomerization and Neu5Ac formation are intended to take place simultaneously in the same system, both enzymes are present at the same time, and it is important that the activities of the enzymes be adjusted to each other, such that roughly equal conversions at the equilibrium are achieved. Taking this into account, a ratio of activities of the two enzymes in the reactor whose value is equivalent to the reciprocal value of the quotient of the respective enzymatic conversion rates is useful.

The starting materials are GlcNAc and pyruvate. The amount of GlcNAc has a dominating function. The molar concentrations of GlcNAc present in the reactor should be at least comparable to the amount of pyruvate. It is preferable, however, to use an excess of GlcNAc in comparison with pyruvate. Large excesses of pyruvate should be avoided since the epimerase is inhibited by pyruvate.

The Neu5Ac formed is, in accordance with the precision of the equilibrium, subject to more or less strong renewed cleavage by the reverse reaction. Although this reaction is inhibited by an excess of pyruvate (see FIG. 4), it appears advantageous continuously to pass reaction medium from the EMR over an ion exchange column and recycle the rest into the reactor. Alternate use of two columns is advantageous.

Figure 6:
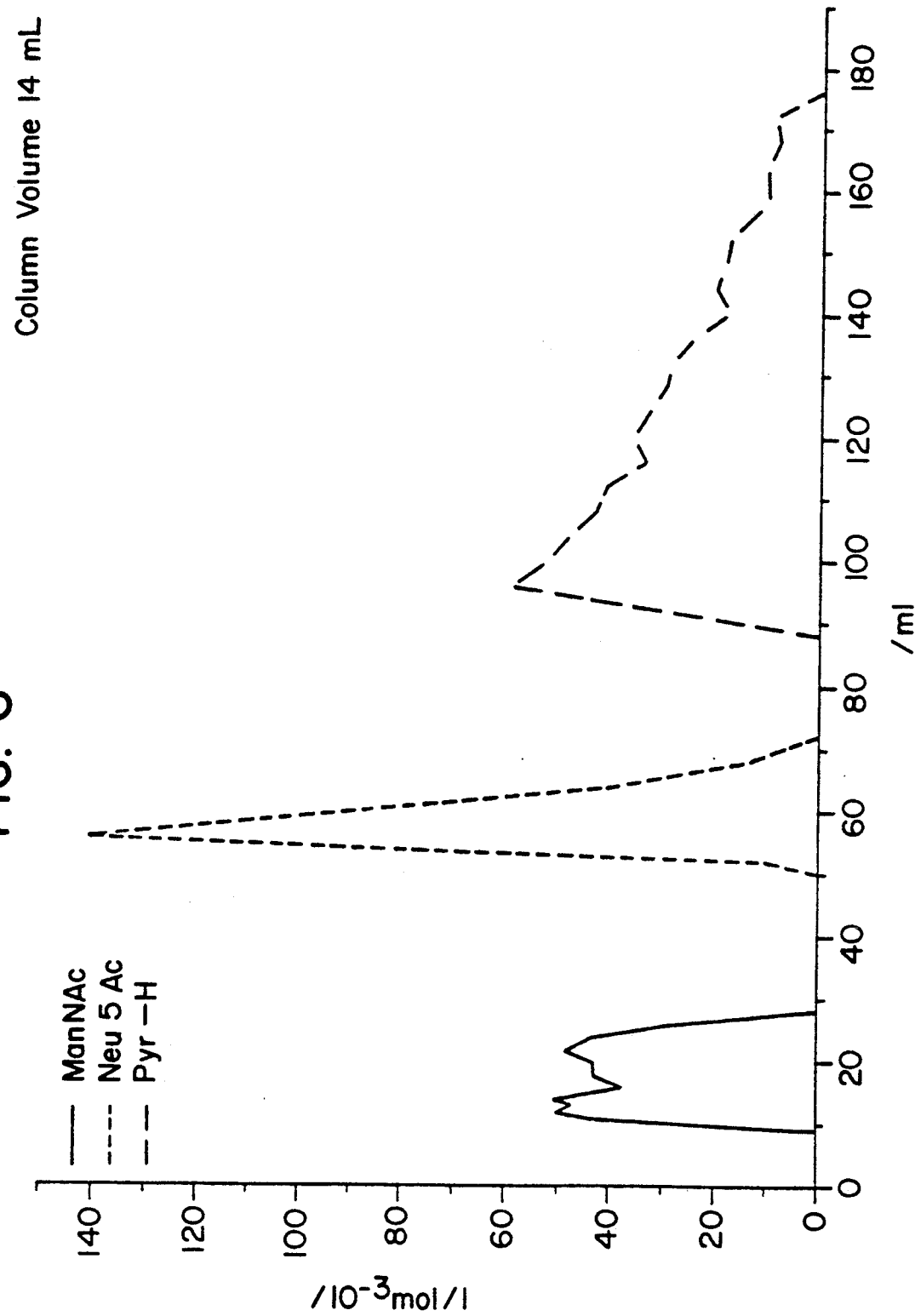
FIG. 6 shows the elution characteristics of ManNAc, Neu5Ac and Pyr/H on an anion exchange column.

As FIG. 6 shows, Neu5Ac is more strongly retained on an anion exchange column (Dowex 1×2, formate, 25° C.) than ManNAc and can thus be concentrated on the column. Pyruvate which has likewise been bound must be replaced accordingly. Residence times of 0.2 −10 h, in particular of about 4 h, appear to be useful for the optimized entire conversion.

In view of the broad pH range found for tuned reactions, as can be seen from FIGS. 1 and 2, the process can be carried out without significant losses of activity at between pH 6 and 8. This broad range facilitates carrying out a continuous operation without using buffer substances since small variations in the pH hardly affect the conversion achieved. Dispensing with buffer substances is desirable since working up is facilitated thereby.

Buffer substances normally are ionic compounds which are also bound by the anion exchanger used for the isolation of the product and have to be separated by suitable chromatographic conditions. A typical chromatogram is shown in FIG. 6. An anion exchanger Dowex 1×2, formate form, was used. Formic acid, 1 mol/l, served as eluent. The column was scaled up by a factor of 8 with the separation power being maintained.

Example of the enzyme-catalyzed production of N-acetyl-neuraminic acid in an enzyme membrane reactor

| Inflow concentrations of the substrates | |
| --- | --- |
| N-acetylglucosamine | $200 \cdot 10^{-3}$ mol/l |
| Na-pyruvate | $100 \cdot 10^{-3}$ mol/l |
| ATP | $5 \cdot 10^{-3}$ mol/l |
| MgCl$_2$ 6H$_2$O | $5 \cdot 10^{-3}$ mol/l |

The substrates are dissolved in water and adjusted to a pH of 7.2 using dilute sodium hydroxide solution.

| Enzyme concentrations in the reactor | |
| --- | --- |
| Epimerase | 11.9 mg/ml |
| Lyase | 3.4 mg/ml |
| Operating conditions | |
| Temperature | 25° C. |
| pH 7.2 to 7.5 at the reactor outlet | |
| Reactor volume | 12 ml |
| Residence time | 2.85 h |

Result

The following concentrations are measured at the reactor outlet:

| N-acetylneuraminic acid | 35 mmol/l |
| --- | --- |
| N-acetylmannosamine | 20 mmol/l |

A conversion of 35% is achieved with respect to the Na-Pyr employed. The space-time yield for N-acetylneuraminic acid is 109 g/(l.d).

What is claimed is:

1. A process for preparing N-acetylneuraminic acid, comprising the steps of:
   (a) isomerizing N-acetylglucosamine in a reactor, in the presence of N-acylglucosamine-2-epimerase (E.C. 5.1.3.8), to give N-acetylmannosamine, and
   (b) reacting the N-acetylmannosamine with pyruvic acid in the presence of N-acetylneuraminic acid pyruvate lyase (E.C. 4.1.3.3) in the same reactor to give N-acetylneuraminic acid, wherein both the epimerase and the lyase are present in a reactor simultaneously, and steps (a) and (b) occur simultaneously.

2. The process as claimed in claim 1, wherein the conversion is carried out continuously.

3. The process as claimed in claim 2, wherein the conversion is carried out in an enzyme membrane reactor using an ultrafiltration membrane having a cut-off greater than or equal to 1,000.

4. The process as claimed in claim 1, wherein the epimerase and the lyase are present in the reactor in a ratio of activities which is equivalent to the reciprocal value of the quotient of the respective enzymatic conversion rates.

5. The process as claimed in claim 1, wherein an excess of N-acetylglucosamine in the reactor is maintained relative to pyruvate.

6. The process as claimed in claim 1, additionally comprising the steps of passing the reactor outflow through an ion exchange column to separate the N-acetylneuraminic acid, and recycling the rest of the outflow into the reactor.

7. The process as claimed in claim 1, wherein the pH in the reactor is about pH 7.5 and the temperature in the reactor is about 25° C.

8. The process as claimed in claim 3, wherein mean residence time in the reactor is about 0.2–10 hours.

9. The process as claimed in claim 3, wherein mean residence time in the reactor is about 4 hours.

* * * * *